(12) United States Patent
Jori

(10) Patent No.: US 7,422,694 B2
(45) Date of Patent: Sep. 9, 2008

(54) PROCESS FOR THE MICROBIOLOGICAL DECONTAMINATION OF WATER BY MEANS OF PHOTOSENSITIVE AGENTS

(75) Inventor: Giulio Jori, Padova (IT)

(73) Assignee: Salbert Co., Ltd., Hong Kong (CN)

( * ) Notice: Subject to any disclaimer, the term of this patent is extended or adjusted under 35 U.S.C. 154(b) by 362 days.

(21) Appl. No.: 10/493,239

(22) PCT Filed: Oct. 21, 2002

(86) PCT No.: PCT/EP02/11748

§ 371 (c)(1),
(2), (4) Date: Jun. 15, 2004

(87) PCT Pub. No.: WO03/035553

PCT Pub. Date: May 1, 2003

(65) Prior Publication Data

US 2004/0245183 A1 Dec. 9, 2004

(30) Foreign Application Priority Data

Oct. 23, 2001 (IT) .......................... VR2001A0110

(51) Int. Cl.
*C02F 1/68* (2006.01)
(52) U.S. Cl. ....................... 210/748; 210/764
(58) Field of Classification Search ................ 210/748, 210/764; 514/185
See application file for complete search history.

(56) References Cited

U.S. PATENT DOCUMENTS

| 4,318,883 | A | * | 3/1982 | Polony et al. ................. 422/22 |
| 6,454,951 | B1 | * | 9/2002 | Jori ............................ 210/748 |
| 2002/0103246 | A1 | | 8/2002 | Schaffer et al. |

FOREIGN PATENT DOCUMENTS

DE  19606081 A1 *  8/1997

OTHER PUBLICATIONS

Minnock et al, Photoinactivation of bacteria. Use of a cationic water-soluble phthalocyanine to photoinactivate both Gram-negative and Gram-positive bacteria, Journal of Photochemistry and Photobiology, pp. 159-164, 1996.*

* cited by examiner

Primary Examiner—Robert A. Hopkins
(74) Attorney, Agent, or Firm—Nixon & Vanderhye P.C.

(57) ABSTRACT

Cationic phthalocyanine and/or porphyins salts are used as photosterilising agents for microbiologically contaminated waters, particularly for inactivating Gram-positive and Gram-negative bacteria, yeasts, micoplasmas and parasites. Synergistic action for water photosterilisation by the simultaneous use of the cationic phthalocyanine salt and a porphyrin molecule, which performs its photosterilising action by a mechanism identical with that typical of phthalocyanines, and whose visible light absorption spectrum efficiently complements the absorption of phthalocyanines. The photosterilising salts can be added to the water as a solution, or as a powder or tablet.

1 Claim, 5 Drawing Sheets

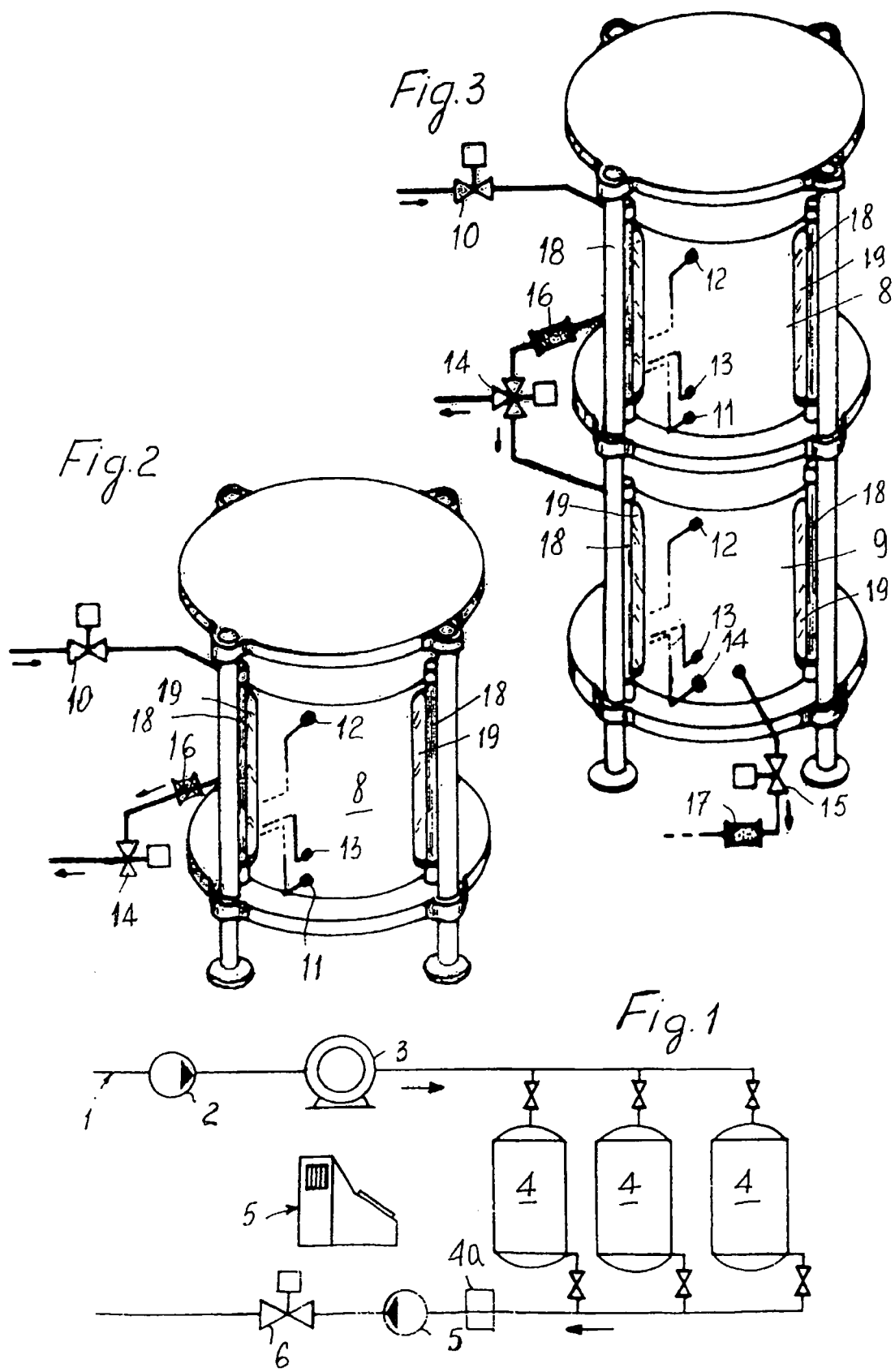

PROCESS FOR THE MICROBIOLOGICAL DECONTAMINATION OF WATER BY MEANS OF PHOTOSENSITIVE AGENTS

This application is the US national phase of international application PCT/EP2002/011748 filed in English on 21 Oct. 2002, which designated the US. PCT/EP2002/011748 claims priority to IT Application No. VR2001A000110 filed 23 Oct. 2001. The entire contents of these applications are incorporated herein by reference.

The present invention relates to a method which allows an efficient decontamination of microbiologically polluted water by means of photosensitive agents. More particularly, the present invention relates to the use of cationic phthalocyanine (Pcs) derivatives as such, as well as through a possible combination thereof with porphyrins, as photosensitive agents to decontaminate and sterilise waters contaminated by pathogenic agents of microbial nature, e.g. Gram-positive and Gram-negative agents, yeasts, micoplasmas, parasites and fungi.

Water decontamination from pollutants of microbiological nature is a cause of major concern in several parts of the world, not only in developing countries, but also in the geographical areas surrounding the Mediterranean Sea, where according to the conclusions drawn by the European Community Scientific Commission, a real danger exists of a severe shortage of water resources within the next thirty years (see the volume "Euro-Mediterranean S&T Cooperation", 1997, issued by the DGXII—Section INCO-DC of the European Union).

This expected water scarcity will not only involve drinking or irrigation water, but also water used in fields such as fish-farming, a practice more and more widely expanding, particularly in the Mediterranean region, on account of the ongoing impoverishment of its wild fish fauna. For this reason, several methods were adopted and studies and experimental researches have been undertaken or are still currently underway, to assess the feasibility of treatments aimed at the decontamination of waters from pollutants of both chemical and biological nature. The methods brought forward or available so far, particularly those aimed at treating and decontaminating microbiologically polluted waters, can be summarised and categorised as follows:

a) Water Heating by Exposure to Very Bright Sunlight.

This method, which is advantageously cost effective and has little effect on the environment, has the obvious limitation to be suitable for being applied only to water systems exposed to solar radiation for sufficiently long periods of time, and to strongly rely on weather conditions which are inherently unpredictable. Moreover, normally reachable temperatures under such conditions (60-70° C.) are not high enough to cause inactivation of many heat-resistant microbial species. (Reference is made to the pamphlet part of "Science, Research and Development", published by Wallingford Oxon OVERSEAS development unit, EU publisher, page 71, 1997)

b) Water Filtration Through Sterilising Filters or Adsorbent Mafter (e.g. Sand)

Although this method is itself very effective when based on filters provided with pores having a suitable size for obstructing microbial cell passage, it is expensive, and limited to treatment of quite small quantities of water. Nevertheless, filters based on sand, animal charcoal and other adsorbent matter have smaller sterilising capabilities and can only partly decrease the size of the microbial population. (See Xanthoulis D, Guillaume Ph. "La valorization des eaux residuaires de l'usine de surgelation", AGROPHORA, Athens, 1994).

c) Combined Application of Hyperthermia and Anaerobiosis.

The combination of two different techniques certainly enhances the attainable sterilization level; however, the water deoxygenation process is long and can be efficaciously applied only to limited volumes of liquid. Moreover, such a technique has only a limited effect on the several strains of bacteria that can proliferate in anaerobiotic environments. (See Sanroman et al. "Immobilisation of *Aspergillus niger* and *Paenerochete Chrysosporium* on polyurethane foam", in: Immobilised Cells Basics and Applications, Elsevier Science Publisher, pp. 32-135, 1995).

d) Titanium Dioxide Catalysed Photodecontamination.

Titanium dioxide is a highly effective, rapidly acting photosensitising agent. However, this compound is activated by irradiation with light wavelengths in the near ultraviolet (about 350 nm) region, which has firstly a limited water penetration power, particularly if the water is relatively cloudy, thus reducing the sterilisable volume thereof per unit of time; secondly, it is directly absorbed by the genetic material of the microbial cells, entailing an induction of mutagenic effects and a gradual selection of photoresistant microbial species (See Balcioglou I. A, Inel Y., "Photocatalitic degradation of organic contaminants in semiconductor suspensions with added hydrogen peroxide", J. Environ. Sci. Health A3 (1): 123-138, 1996)

e) Direct Irradiation with Ultraviolet Light.

Because this approach relies on the properties of some ubiquitous constituents of cells and tissues (such as nucleic acids and proteins) to efficiently absorb ultraviolet light, it entails several unwanted side-effects, such as its high cost, and the sophisticated technology needed for the operation of ultraviolet light sources, the limited capability that these radiations, above all those at shorter wavelengths, have to penetrate in depth into water, and the mutagenic action exerted by these radiations that cause genetic mutations in the cells and a selection of photoresistant species (See Pousset T., "Possibilités d'alimentation des décharges haute pression par les alimentations de résonance. Comparaison avec d'autres modes d'alimentation". Thèse de l'Universitè Paul Sabatier, Toulouse, 1996).

f) Chlorine or Chlorodioxide Based Treatment.

The oxidising action exerted by chlorine is certainly lethal for the great majority of pathogenic agents of microbial origin. The application of this technique on a large scale is limited by the likelihood of secondary actions exerted by chlorine on higher organisms, particularly the irritating effect on skin and eye tissues. Moreover, there are increasing concerns relating to the consequences of such a high concentration of chlorine and chlorine sources, e.g. sodium hypochlorite for the environment.

g) Treatment Based on Wide Spectrum Antibiotics.

This technique is currently being used only in specific cases (e.g. in intensive fish-farming) because of the high cost that it involves, which makes it unsuitable for treating large volumes of water. Moreover, this type of treatment is associated with the high risk that it brings about of inducing a selection of antibiotic-resistant microbial species, which, besides forestalling an efficient water sterilisation, may be a cause of real threat to several ecosystems (and to man) through the spreading of epidemics that are difficult to treat.

h) Photosensitisation Through Visible Light and Porphyrins Bound to an Inert Matrix Visible light, which is inherently non-toxic to microbial cells, becomes highly toxic if it is associated with the action of a photosensitiser, e.g. porphyrins which, once activated by visible light irradiation, generate highly reactive cytotoxic species. The process based on the combined (synergistic) action of light and the photosensitiser has the following advantages:

1) visible light can penetrate water to considerable depths, it is cost-effective and only a simple and straightforward technology is required for its production.
2) the cytotoxic action exerted by photoactivated porphyrins concentrates at the level of the cytoplasmic cell membrane with no involvement of the genetic material, therefore it does not promote the selection of microbial strains which are resistant to photosensitisation. Porphyrins are also natural products and their use does not yield any significant environmental pollution. (See patents No.'s DE-19 962 505 and WO-97/29 636)

Finally, it should also be understood that the prior art mentioned under above point (h) relates to porphyrins and their derivatives, e.g. chlorins and phthalocyanines, covalently bound to inert substrates such as resins, gels and polymers. The limited mobility of the porphyrins bound to these matrices drastically reduces their efficiency as photosensitisers, since it strongly decreases their flexibility affecting their orientation in space and interaction with the cellular membranes themselves, and, above all, it prevents the penetration of the photosensitising agent to the innermost regions of the cell membranes, which represent the most critical sites for cell survival. Accordingly, the damage suffered by photosensitised cells is limited to rather superficial levels thereof, and may not get to be lethal.

As mentioned above, it was previously suggested that microbial cells may be inactivated to different extents by irradiation of visible light having a suitable wavelength, in the presence of photosensitisers. Photosensitisers are generally typified by polycyclic compounds that are activated to an excited electronic state, upon absorbing a photon carrying the suitable energy. Once promoted to an electronically excited state, the photosensitising agents initiate a series of photophysical, photochemical and photo-biological events that can cause irreversible damage to most biological systems. Among the various classes of photosensitisers, a key role is played by derivatives containing the tetrapyrrolic macrocyclic group, e.g. porphyrins, chlorines and phthalocyanines, since these compounds have strong absorption bands in the red region of the visible spectrum (600-800 nm), and can therefore be electronically excited by the absorption of radiation having wavelengths with a high penetration power into several mammalian tissues, and other systems, e.g. water. Accordingly, using these radiations, an even illumination (and photodamage) through considerable volumes of the target system can be obtained.

The main object of the present invention is to provide a microbiological sterilisation process by means of photosensitisers having markedly better photosensitisation and phototoxicity characteristics than similar systems of the prior art. More precisely, the present invention aims at (a) the utilization of photosensitisers with full flexibility of interacting with, orientiating themselves at, the surface of, and penetrating into microbial cells thereby enhancing the overall efficacy of the photoprocess; and (b) the use of photosensitisers with optimal light-absorption characteristics, thus reducing the dose of photosensitiser and the dose of light required to achieve a satisfactory level of water sterilisation.

A further object of the present invention is to use photosensitisers designed to be obtained at extremely competitive costs on account of their production, following synthetic pathways and by work-up processes that are significantly simpler than those required for the photosterilisation systems known so far.

Another object of the present invention is to provide highly structurally versatile (variable) photosensitisers for the preparation of "engineered" photosensitisers, i.e. photosensitisers having a chemical structure designed to obtain specific and predetermined physico-chemical properties for aimed uses that are remarkably better than those typical of the similar systems known so far.

These and other objects that will be better apparent below are attained by a process for sterilising microbiologically polluted water, by means of at least one photosensitising agent according to the present invention which as a photosensitisable agent comprises at least one cationic phthalocyanine having the following general formula whose backbone comprises:

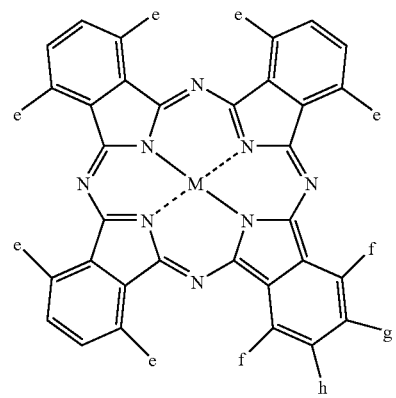

where M is a non-paramagnetic metal ion chosen in the group of Zn (II), Mg (II), Al (III), Si (IV), Ge (IV), Sn (IV), Pd (II), Ca (II), La (III); Ga (III), e, f, g and h can be H or a substituent formed by an alkyl chain having varying length, containing one or more functional groups located either in the backbone or in a specifically added substituent; such functional groups including heteroatoms of which at least one is cationic, and has preferably one or more of the following structures:

of the anilinium type

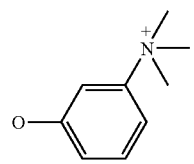

of the pyperidinium type

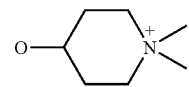

of the alkyl-ammonium type

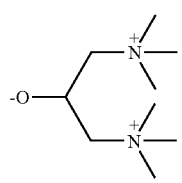

of the morpholinium type

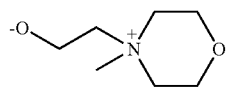

of the pyridinium type

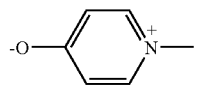

The various cationic substituents are neutralised by monovalent counter-ions e.g. chloride, bromide, iodide, nitrate and toulene-sulphonate.

The cationic substituents can be positioned on two or three adjacent isoindole rings, whereas the substituents on the other rings can comprise hydrogen atoms or non-cationic hydrophobic groups chosen in the group of phenol, $C_0$-$C_{12}$ alkyl groups, rings of the phenyl, pyridine and piperidine type, thus forming an amphiphilic molecule.

Phthalocyanines are chemical compounds with photosensitizing and phototoxic characteristics similar to those of porphyrins. However, phthalocyanines have some important advantages as compared with porphyrins, namely firstly they are obtained by markedly simpler chemical synthetic pathways and work-up processes, which result in an at least five-fold cost reduction, and secondly, but not less importantly, an enhanced structural versatility (variability) that makes it possible to prepare "engineered" phthalocyanines in order to endow them with specific and predetermined chemical and physical properties aimed at very specific and targeted uses (see F. H. Moser, A. L. Thomas, The phthalocyanines, CRC Press, Boca Raton, 1983).

However, the simultaneous use of phthalocyanines in combination with porphyrins can be envisaged, particularly of porphyrins having a chemical structure that is suitable for imparting them with the above mentioned amphiphilic characteristics, as these are meant above. In this respect, a significant example is hematoporphyrin, whose tetrapyrrolic, octa-substituted structure has the following formula:

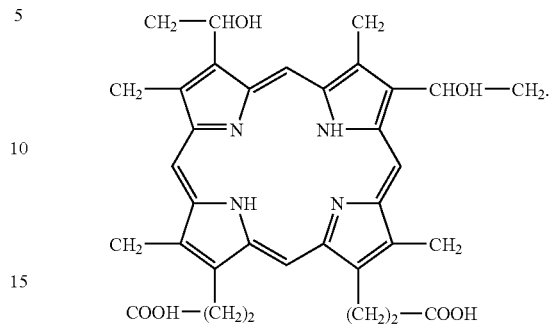

The presence of two secondary alcohol groups and two carboxylic groups adds some hydrophobicity features to the inherently hydrophobic structure of the tetrapyrrolic macrocycle. Hematoporphyrin was actually proven to be a highly effective photosensitiser when causing the inactivation of a wide spectrum of pathogenic agents of microbial nature (G. Jori, PDT for the treatment of microbial infections. *Photodynamics News* 2:2-3, 1999).

The advantage of a combined phototoxic action of cationic phthalocyanines and porphyrins is especially substantiated by the following:

a) In the red region of the visible spectrum (also characterized by a great penetration power into the water) phthalocyanines exhibit a markedly higher visible light absorption efficiency (ten-fold as compared with porphyrins) which allows one to obtain comparable photosensitising effects using a ten-fold lower photosensitiser dosage, and great energy savings;

b) However, phthalocyanines do not absorb wavelengths in the blue (400-450 nm) and green (500-550 nm) regions of the visible spectrum to a significant extent; on the other hand, in these spectral regions porphyrins exhibit strong absorption bands. Accordingly, the simultaneous use of cationic phthalocyanines and porphyrins, such as hematoporphyrin, provides an optimal photoactivation efficiency, above all when the light used is sunlight, or the light source is a halogen or tungsten filament lamp emitting over the whole visible light spectrum. These latter light sources are generally cost-effective, and simple to use.

It should also be understood that phthalocyanines and porphyrins act by the same mechanism towards microbial cells, and particularly their photosensitising action is based on the photogeneration of oxygen reactive species localised at the cytoplasmic membrane level, with the consequent absence of mutagenic effects and development of photoresistant microbial species owing to the lack of involvement of the genetic material. This feature allows one to repeat the photosterilising procedure several times, if necessary.

Since phthalocyanines and hematoporphyrin are free to move in the aqueous medium, and to interact with the cells to an optimal extent, the photoprocess that they promote is not subjected to the above discussed limitations given under paragraph (f).

More in detail, phthalocyanines are tetraisoindole derivatives and make up a very large class of structurally versatile (variable) compounds—see formula 1—through the coordination of one metal ion at the centre of the macrocycle and/or the introduction of 1 to 8 suitable substituents at peripheral points of the macrocycle. Phthalocyanines are an excellent class of biological photosensitisers and as such, several different applications have been found for them in the medical field, e.g. in the photodynamic anti-tumour therapy and in preventing restenosis affecting arteries undergoing angioplasty.

Phthalocyanines are also characterised by a high phototoxic activity towards a wide range of microbial cells, including both Gram-negative bacteria (which are generally unaffected by several types of treatments on account of the structural complexity of the wall enveloping their cells) and antibiotic-resistant strains (e.g. *Staphylococcus aureus*, meticillin-resistant and vancomicin—resistant strains). The latter are a cause of growing concern worldwide, because they are spreading at an ever increasing rate.

In the antimicrobial field, the phthalocyanines that seem to exhibit an optimal photosensitising efficiency are those coordinated with diamagnetic metal ions, i.e. Zn (II), Mg (II), Al (III), Si (IV), and peripherally functionalised with positively charged groups, e.g. N alkyl-pyridine groups, where R is an alkyl chain, e.g. comprising a $C_1$-$C_{22}$ chain, N,N,N-trialkyl aniline groups, piperidine groups where N is quaternary and quaternary alkyl amino groups. In any case, quaternarisation is carried out by alkyl group substitution, as shown above.

Hematoporphyrin exhibited phototoxicity towards wild and antibiotics-resistant bacterial strains (e.g. *Streptococcus* and *Staphylococcus* strains) as well as towards yeasts (e.g. *Candida* strains).

The practical implementation of the sterilisation process of the several types of water can be carried out adopting two different procedures:

a) direct addition of phthalocyanine aliquots, optionally combined with hematoporphyrin, depending on the desired dosage, to the liquid phase to be sterilised, in powder, tablet form, or as a solution with a known titre;

b) addition of phthalocyanine, optionally in combination with hematoporphyrin, into an irradiation chamber positioned outside the system to be sterilised.

Phthalocyanines and porphyrins added to water and subsequently subjected to irradiation may undergo a partial degradation with by-product formation. Drawing on the results of the experiments carried out by the applicant, the by-products do not exhibit any significant toxicity.

To this end, phthalocyanine aqueous solutions subjected to irradiation and degraded by 90% have been additioned in the dark to human cell suspensions (fibroblasts and keratinocytes) and no decrease in cell viability was observed even after a prolonged incubation.

The irradiation chamber technique is also illustrated in the accompanying tables of drawings, in which:

FIG. 1 is a diagrammatic view of an open cycle sterilisation plant;

FIG. 2 shows a diagrammatic view of a closed cycle sterilisation plant;

FIG. 3 illustrates a double irradiation chamber suitable for being used in the sterilisation plants shown in FIGS. 1 and 2;

In the accompanying drawings, the same or similar parts or components are indicated at the same reference numerals.

Figure 4:
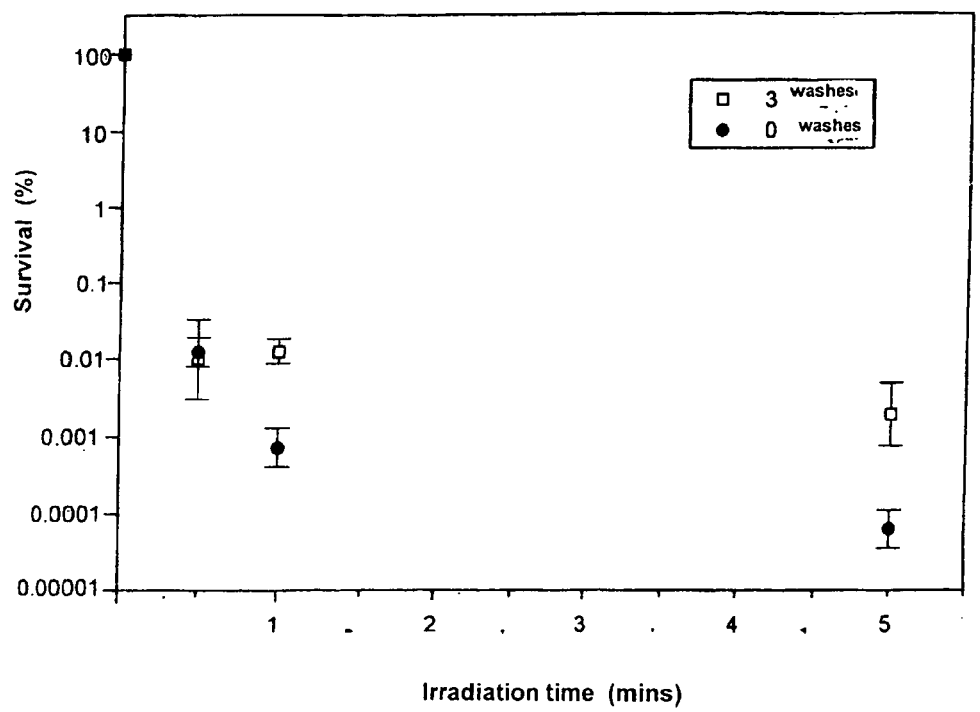
FIG. 4 is a photoinactivation graph of a *Staphylococcus aureus* strain.

The diagrammatic view shown in FIG. 1 of the plant for carrying out an open cycle sterilisation process, e.g. the sterilisation of the water feeding into a humidification vessel, or a swimming-pool, or a fish-farming tank, comprises a feeding inlet 1 provided with a respective pump 2, a mechanical filter or a bank of mechanical filters 3 designed to retain any bulky matter, including organic matter, one or more irradiation chambers 4, where a plurality of light sources are provided, a filter 4a downstream from the vessels or irradiation chambers 4, and optionally at least one or more pressure pumps 5, an outlet valve 6, and a programmable control unit 7.

It should be understood that, besides closed vessels, the irradiation chambers 4 can further comprise a pool or a tank, e.g. a fish-farming tank, a well or the like.

In the closed cycle sterilisation plant embodiments shown in FIGS. 2 and 3, the irradiation chamber(s) only comprise(s) one single chamber 8, or two chambers 8 and 9, connected to each other in cascade (in series).

In the embodiment comprising two chambers, chamber 8 can be positioned above chamber 9 and, like chamber 9, be provided with an inlet electrovalve 10, a lower capacitive sensor 11, and an upper capacitive sensor 12 to check for the presence of liquid to be treated and possibly the level thereof in the said chamber, with a LED (light emitting diode) 13 to control light absorption and thus signal the presence of phthalocyanine and/or hematoporphyrin, that mainly absorbs in the red visible light region, with an outlet electrovalve 14 and 15 respectively, with a sand filter 8 (or other adsorbant matter) 16, 17 to retain phthalocyanine and, possibly, hematoporphyrin or other porphyrins, and with irradiation lamps 18 which are positioned within or at one or more ports 19 suitable for being controllably closed and provided on the walls of chambers 8 and 9.

The outlet electrovalve 14 is a three-way valve to provide both a discharge valve from chamber 8, and a connection element to the chamber 9 inlet. Filters 16 and 17 are designed to absorb and retain phthalocyanine and possibly hematoporphyrin before the photosterilized liquid (water) is fed back into the tanks or vessels 8, and they can comprise anionic resins, e.g. carboxylic and sulphuric resins, onto which the cationic phthalocyanines bond, and/or adsorbant matter having a policyclic structure, e.g. zeolites, or activated animal charcoal.

The phthalocyanine and hematoporphyrin concentration in the water subjected to photoprocessing can be quantitatively determined in real time both at the beginning of the treatment and after various irradiation periods of time by means of spectroscopic techniques, e.g. absorption spectrophotometry or spectrophotofluorimetry.

The irradiation chambers or vessels 8 and 9 are connected to each other and fluidly in communication, and they rely on the biocidal action exerted by phthalocyanine activated by visible light. Water is mixed with phthalocyanine and/or hematoporphyirin in chamber 8, affording a homogeneous solution, that is subsequently irradiated with light by means of lamp units that are suitably positioned therewithin. Chamber 9 contains sterilized water and therein it is made available for use.

The treatment steps are in the following sequence: the water to be treated is fed into vessel 8 through the inlet electrovalve 10 until the vessel is full. The water level in the vessels is monitored by capacitive sensors 11 and 12, respectively, positioned at the top of the vessel, and at a lower position thereof. Once the liquid level has reached the level of the upper capacitive sensor 12 the electrovalve 10 stops the water flow at the inlet.

Simultaneously, a measuring device (not shown), within vessel 8, suitably loaded with phthalocyanine and/or hematoporphyrin in solid powder, tablet form, or as a liquid or semi-liquid solution, releases predetermined quantities of phthalocyanine. The amount of phthalocyanine is further monitored by diode 13, which measures light absorbance of the phthalocyanine and/or hematoporphyrin aqueous solution. As it is usual in the case of phthalocyanine, the absorption wavelength is within the red spectral region (600-800 nm). In case hematoporphyrin is added, both the same light source, and a wide visible electromagnetic radiation emission spectrum source (tungsten lamp or a fluorescent lamp) can be used. Diode 13 signals whether the measuring device is out of order by checking for a shortage or an excess of phthalocyanine; in case of shortage or excess of phthalocyanine, the steriliser is stopped, and the electrovalves are closed.

After a suitable irradiation time, ranging between a few seconds and 60 minutes, by means of the lamp units positioned within vessel 8, the outlet electrovalve 14 is opened so that sterilised water transfer into tank 9 can take place. When the lower capacitive sensor 11 detects that vessel 8 is empty, a signal is emitted by it and sent to the control unit 7 in order to open the inlet electrovalve to allow vessel 8 to be filled up again.

As shown in FIG. 3, whilst the water is being discharged from vessel 8, it flows through the sand filter 16 that retains the phthalocyanine and/or the hematoporphyrin therein contained. Preferably, one diode is provided, e.g. a diode of the same type as diodes 13, adjacent to filter 16, on the outlet side to detect the wear and tear of the filter itself; in fact should the absorbance in the red region detected by the diode exceed a number of specific threshold values (indicating an incomplete adsorption of the phthalocyanine and/or the porphyrin) the filter must be replaced.

Once the treated, hence sterile, water has been poured into vessel 9, the level thereof is checked by capacitive sensors 11 and 12 therein provided which control the charging and discharging of the water through inlet 14 and outlet 15 electrovalves, as it happens in vessel 8.

The sterile water sent into vessel 9 contains no photosensitiser, which underwent photodegradation in vessel 8 and was subsequently retained by the organic filter 16.

Desirably, mainly for additional safety reasons, a bank or set of lamps can be provided, that provide further irradiation of the water contained in vessel 9. A diode 13, which is identical with the diode provided in tank 8, monitors and measures any residual concentration of phthalocyanine and/or porphyrin.

At this stage water is available for its intended use, therefore it is discharged through the outlet electrovalve 15, and next through the filter 17 suitably made of sand or a similar material (e.g. zeolites or activated animal charcoal) in order to adsorb the phthalocyanine and/or porphyrin to make sure that there are no leaks of any photosensitising agent whatsoever into the environment.

A diode, not shown, positioned downstream from filter 17 and of any suitable type, e.g. the same as diodes 13; checks filter 17 for clogging, and for any phthalocyanine and/or hematoporphyrin leaks. Should a phthalocyanine and/or hematoporphyrin leak be detected, the diode would send a signal to control unit 7, and the system would be shut-down immediately.

Thus the cycle can proceed without any flow interruption.

Of course, the above mentioned system is susceptible to several modifications and variations within the protection scope granted to it by the claims. Hence, for example, only one vessel can be used to carry out a wholly discontinuous process through which the required amounts of water are intermittently fed.

Instead a closed cycle plant arrangement (FIG. 2) can provide a better control over residence time in the plant through the actuation of valves 8, 9, 10, and 11, in order to provide an improvement in pathogenic agent inactivation. Advantageously, if possible, sun-light can be used instead of artificial light, as it is the case for open water reservoirs or tanks used for the production of drinking water, for fish-farming or for agricultural purposes.

Generally, as already mentioned above, once they have been activated to an electronically excited state by irradiation with light in the visible region, particularly at a 600-800 nm wavelength, phthalocyanines and/or porphyrin can cause a sudden decrease in viability of several bacterial strains. One typical example is the wild strain of *Staphylococcus aureus*— (Gram-positive bacterium), and its meticillin-resistant variant (MRSA), a wild strain of *Escherichia coli* (Gram-negative bacterium), a typical micoplasm (*Acholeplasma laidlawii*) and a typical epitome of yeasts (*Candida albicans*).

As it can be deduced from the example shown in the following Table 1, the photoinactivating action exerted by phthalocyanines can lead to a decrease of the microbial cell population by a $10^5$ factor (corresponding to a 0.001% of the initial cell concentration), using relatively mild irradiation protocols, e.g.

a) phthalocyanine concentration in the micromole range;
b) photosensitiser-cell incubation time equal to a few minutes (1 to 5 minutes)
c) irradiation with light fluence-rate not higher than 100 $mW/cm^2$, and with overall light dosages not higher than 80 $J/cm^2$ corresponding to irradiation time of max 15 minutes.

Usually, the positive charges on the phthalocyanine molecules are neutralized by counterions, e.g. chloride, bromide, iodide or p-toulenesulphonate. The phthalocyanine photoactivation can be accomplished by means of light sources with emission in the visible region of the electromagnetic spectrum, e.g. tungsten filament lamps, quartz-halogen fluorescent lamps or diode arrays. The whole light emission from the lamp can be used as such, or else suitable optical filters can be introduced in the light beam, in order to isolate wavelength ranges corresponding to the light absorption band of the specific sensitiser.

Table 1

Photoinactivation of selected microbial species by visible light irradiation in the presence of phthalocyanines and particularly of phthalocyanines substituted at the "e" and "f" positions in structure 1 with eight positively charged groups of the n-butyl-1-N,N-diethyl, N-methyl-amino type.

Cell survival is expressed on a logarithmic scale and it is referred to non-irradiated microbial cells used as control group whose viability is set at 100.

| MICROBIAL SPECIES | SPECIFIC EXAMPLE | LOG ($S_{irr}/S$) RESIDUAL SURVIVAL |
|---|---|---|
| Gram (+) Bacteria | Staphylococcus aureus Wild Strain | −3.7 |
| | Staphylococcus aureus (Meticillin-resistant) | −3.0 |
| | Staphylococcus aureus (Vancomicin-resistant) | −3.3 |
| Gram (−) Bacteria | Escherichia coli | −2.8 |
| | Vibrium anguillarum | −3.6 |
| Yeasts | Candida albicans | −4.0 |
| Micoplasms | Acholeplasma laidlawii | −4.0 |

Experimental Conditions:

microbial cell concentration in the aqueous suspensions: $10^6$–$10^7$ cells/ml, pH of the medium: 7.4 (0.8% NaCl w/v phosphate-buffered saline)

Incubation and irradiation temperatures: 37±1° C.;

photosensitiser-cells incubation: 5 minutes;

photosensitiser concentration in the incubation medium: 1 µmol/l;

light source: 250 W Osram tungsten filament lamp, used to obtain a light fluence rate equal to 25 mW/cm² at the level of the irradiated cell suspension;

emitted wavelength range: 380-800 nm;

irradiation time: 10 min;

technique adopted for cell viability measurements: clonogenic assay.

FIG. 4 shows a typical photoinactivation plot of meticillin-resistant Staphylococcus aureus and wild strain Staphylococcus aureus, against phthalocyanine concentration whose structure is shown in Table 1, upon irradiation obtained by means of the above described equipment. In the plot, the percent survival is on the y-axis whereas the irradiation time in minutes is on the x-axis, and the system irradiated after 0 washings was compared with the system after 3 washings with phosphate-buffered saline.

Figure 5:
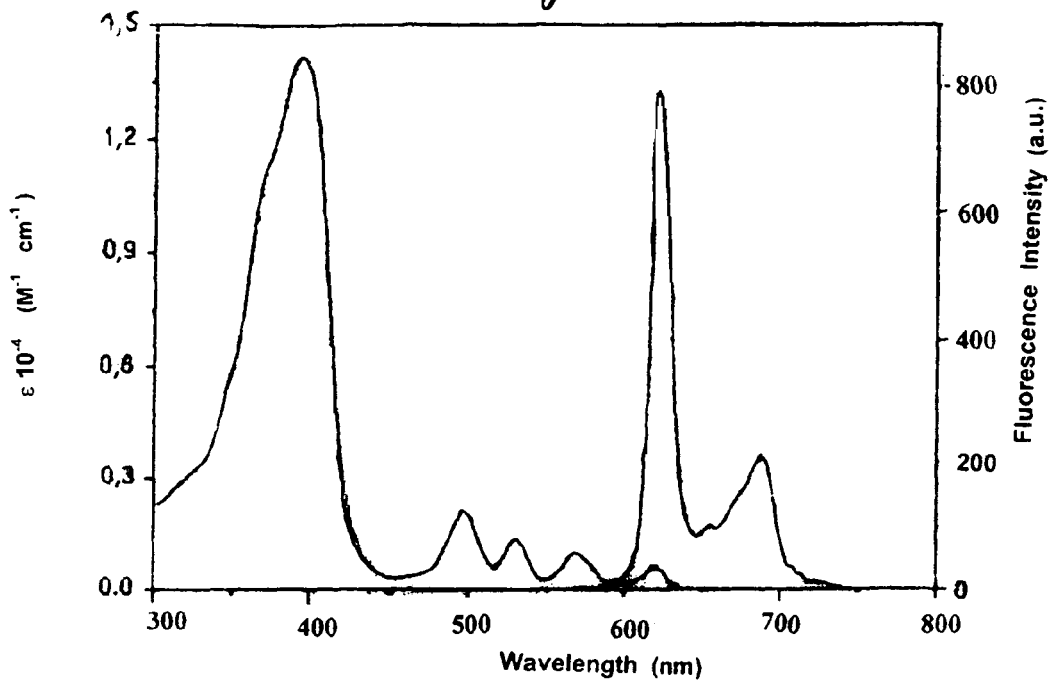
FIG. 5 is a graph showing the hematoporphyrin absorption spectrum in the UV-visible region.

FIG. 5 illustrates the hematoporphyrin (a typical amphiphilic porphyrin) absorption spectrum in the UV visible region of the electromagnetic spectrum. As one can easily note, the spectrum exhibits a strong absorption band in the blue region (380-410 nm) and enhanced bands in the green (480-550 nm) and red regions (600-700 nm).

Figure 6:
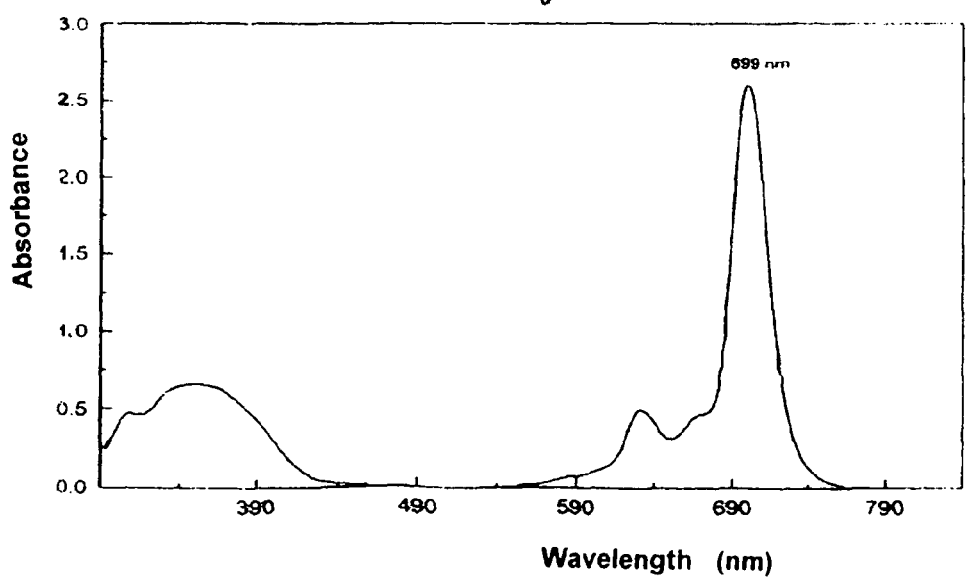
FIG. 6 is a graph showing the zinc-phthalocyanine absorption spectrum in the UV visible region.

FIG. 6 shows the Zinc-phthalocyanine absorption spectrum in the UV/visible region of the electromagnetic spectrum. Absorption bands are seen in the UV-A (320-380 nm) and red (600-700 nm) regions, whereas the absorption in the blue and green regions is not significant.

Figure 7:
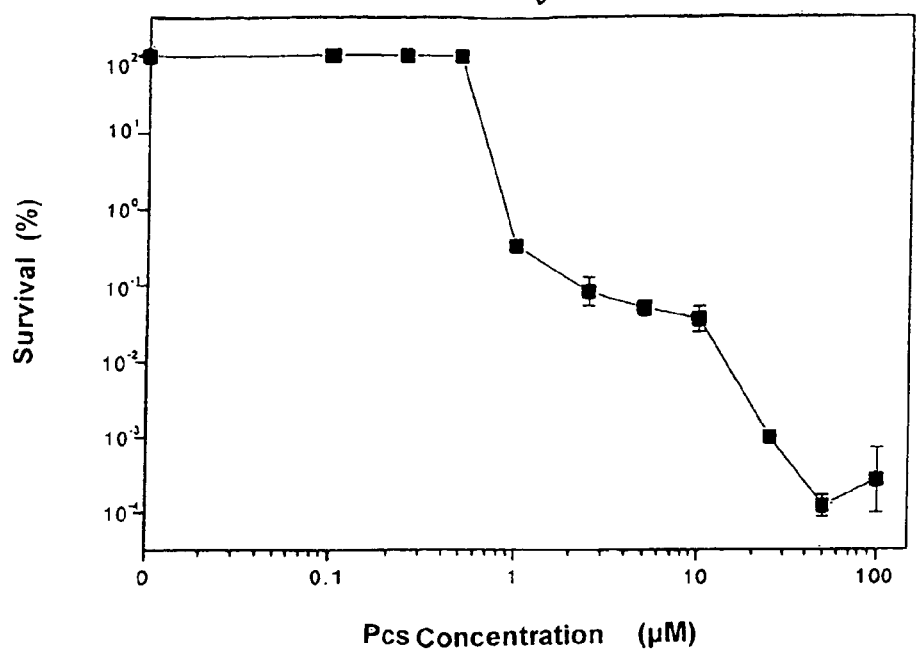
FIG. 7 is a graph showing the effect of an octa-substituted cationic Zinc-phthalocyanine on the viability of *Staphylococcus aureus* cells.

The plot illustrated in FIG. 7 shows the effect exerted by the cationic octa-substituted phthalocyanine on the viability the antibiotic-resistant Staphylococcus aureus cells. The irradiations were carried out in the presence of phthalocyanine having different molarity after 5 minutes of preincubation in the dark. Cell viability was measured by clonogenic assay after irradiation with light having a 600-700 nm wavelength (50 mW/cm²) at 37° C. for 5 minutes.

Figure 8:
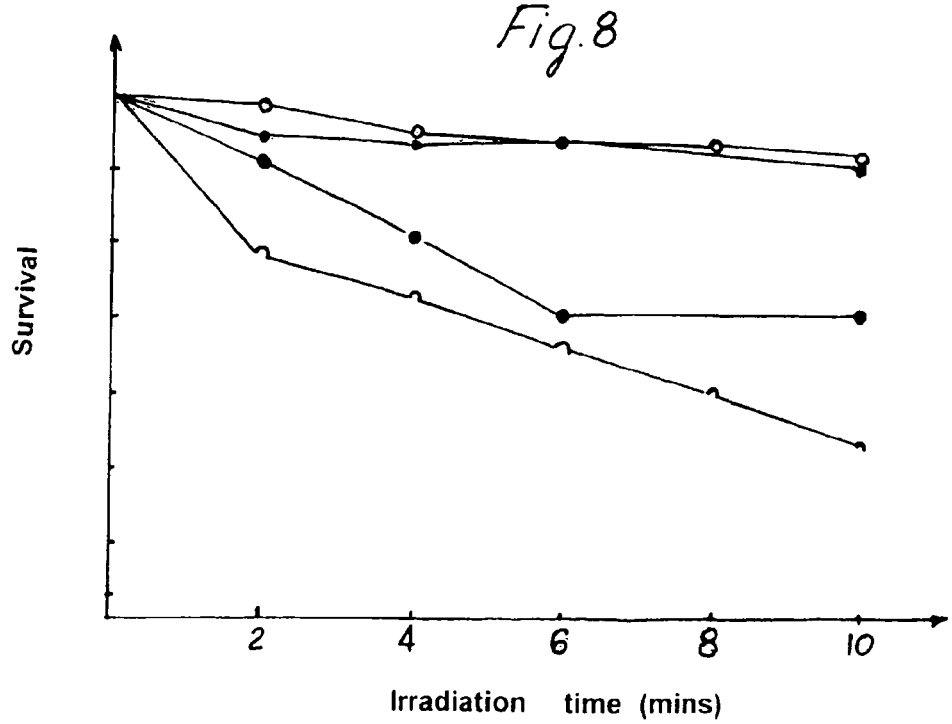
FIG. 8 is a graph showing the decrease in *Staphylococcus aureus* viability plotted against time of exposure to visible light in the presence of hematoporphyrin.

FIG. 8 is a plot where the experimental results relating to the decrease in Staphylococcus aureus viability on exposure to visible light in the presence of hematoporphyrin at 0.1 pg/ml (circles) and 1 µg/ml (squares) concentrations were plotted. Bacterial cells were either in the stationary (closed symbols) or in the logarithmic (open symbols) growth phase. It is clear how effectively this porphyrin photosensitises the inactivation of a highly infective bacterial strain characterised by a rapid development of resistance to antibiotics.

Figure 9:
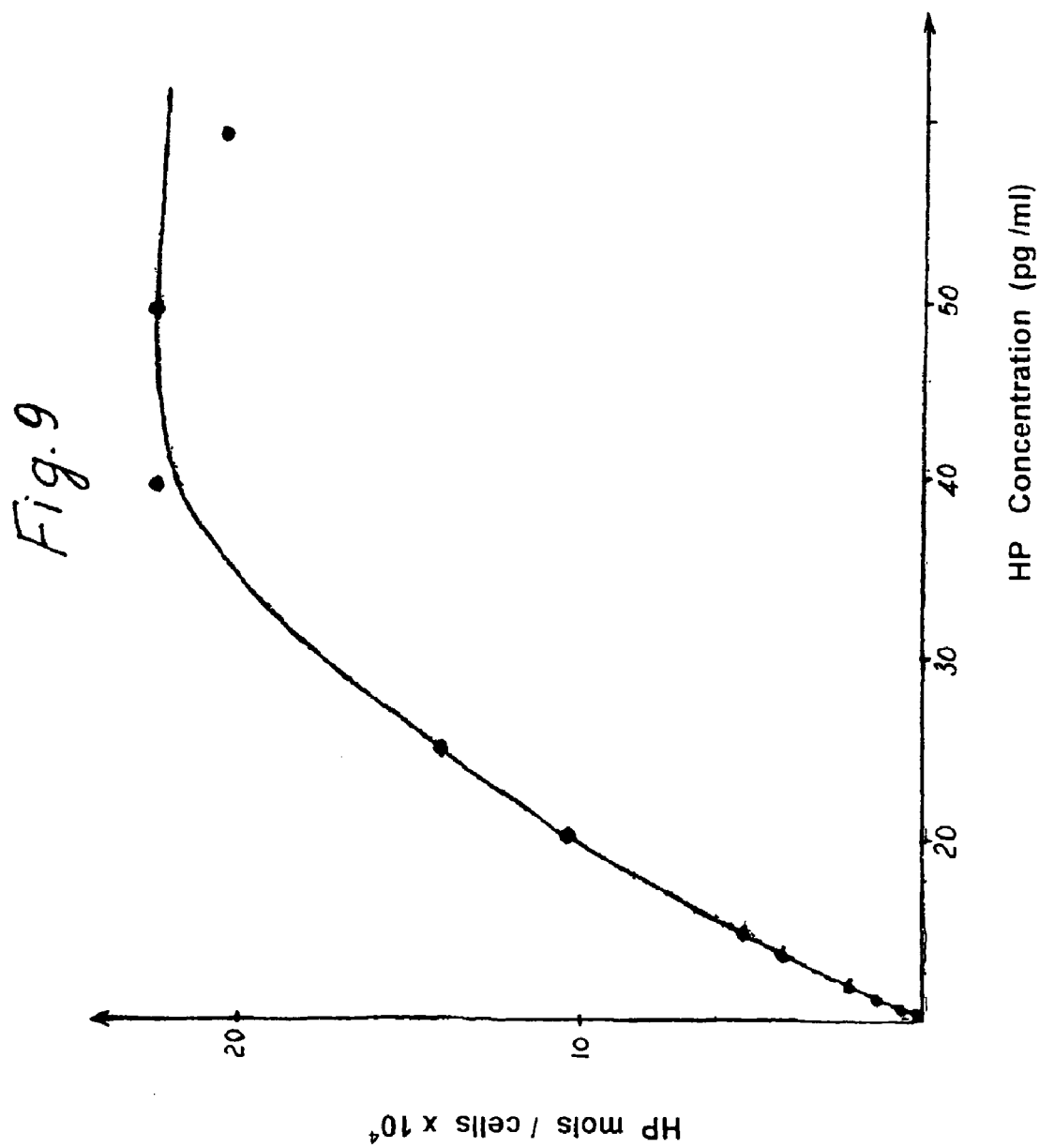
FIG. 9 is a graph showing the capability of hematoporphyrin (HP) to be accumulated by bacterial cells.

The plot shown in FIG. 9 shows the efficiency with which hematoporphyrin (HP) is accumulated by bacterial cells. In particular, the plot shows the effect exerted by the porphyrin concentration on the amount of photosensitising agent, which is bound to cells of a highly infective bacterial strain, e.g. Staphylococcus aureus. In this specific case, the porphyrin-bacterial cell incubation was carried out at room temperature for 6 minutes. The amount of porphyrin bond to Staphylococcus aureus cells was determined by means of fluorescence spectroscopy after extraction of the photosensitising agent from the cells using a chemical method.

The efficiency of cationic phthalocyanines (whose molecules bear from 1 to 8 positive charges) to promote an extensive inactivation of a broad number of microbial cells can be conveniently exploited for water photodecontamination. The characteristics of the phthalocyanine photosensitisation processes, which make them particularly suitable for this application, can be summarised as follows:

induction of a decrease in the microbial population which is as large as at least 5 logarithms by irradiation for short periods of time (I<15 minutes) at a low phthalocyanine (micromoles/liter) concentration;

no detectable toxicity of phthalocyanines towards both animal and plant biosystems at photoactive photosensitiser dosages;

a high solubility of cationic phthalocyanines in water that provides a progressive dispersion thereof into the environment and leading to negligible local concentrations;

possibility to evenly irradiate relatively large volumes of water on account of the great penetration of radiation at the wavelengths used for phthalocyanine photoactivation;

ability of phthalocyanines to cause photoinactivation of pathogenic agents of microbial nature, regardless of their antibiotic-resistance spectrum;

ability of phthalocyanines to damage cells almost exclusively at the membrane level, which results in minimising the risk of triggering mutagenic processes and selecting photo-resistant microbial species;

possibility to use phthalocyanines as photosterilising agents in powder, tablet form, or as a solution, or as a gel or the like form;

possibility to enhance the efficiency of the overall photosterilising process through simultaneous use of phthalocyanines and a suitable porphyrin molecule, such as haematoporphyrin, as photoactivatable antimicrobial agents;

possibility to obtain photosterilisation by means of light sources requiring a straightforward technology, that are cost-effective and do not require the adoption of safety measures for operators and consumers alike, and do not inherently exert any effects on the constituents of the different ecosystems.

Water sterilisation by means of visible light in the presence of cationic phthalocyanines possibly associated with hematoporphyrin can be practically implemented in the following fields among others:

fish-tanks and artificial lakes, using in-built light sources in the former case, and sun-light for phthalocyanine photochemical activation in the latter;

drinkable water preferably by irradiation of already treated water, e.g. by ozone treatment aimed at degrading chemical pollutants; the irradiation can be performed immediately before filtering the water through a column positioned upstream from the mains feeding inlet;

irrigation water to be used in the agricultural field;

water collected in large tanks for its subsequent use as drinking or irrigation water: in this case a synergistic action of sun-light and artificial light is preferred;

recycled and waste water for industrial uses, in order to decrease the microbial population and minimize the effects of other phenomena, e.g. rusting, debris deposition build-up and the like, corrosion, and so on;

sterilisation of surgical or, more generally, biomedical instruments previously immersed in a phthalocyanine/porphyrin aqueous solution which is placed in vessels equipped with visible light sources;

aquaculture, preferably intensive fish- and shellfish— farming, in order to reduce the microbial population and inhibit algal and fungal growth, with or without a limited use of the currently used biocides;

treatment to reduce bacterial proliferation and algal growth in the nautical, industrial and building fields;

in infected waters to control the spreading of potential pathogens, e.g. microbes, larvae and parasites.

The invention claimed is:

1. A method of photosterilizing microbiologically contaminated water which comprises (a) adding to the microbiologically contaminated water a photochemically effective amount of two or more photosensitive and phytotoxic agents selected from a phthalocyanine and a porphyrin or salts thereof in either free base or diamagnetic metal ions-coordinated form, and thereafter (b) exposing the water of step (a) to a photosensitizing dose of irradiation to photosterilize the microbiologically contaminated waters; wherein the porphyrin agent comprises hematoporphyrin having an octa-substituted tetrapyrrole structure having the following general formula:

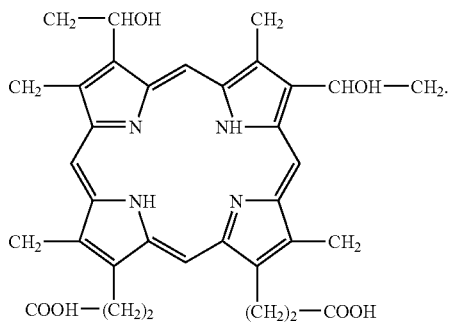

* * * * *